United States Patent
Roger-Dalbert et al.

(10) Patent No.: US 7,270,978 B2
(45) Date of Patent: Sep. 18, 2007

(54) **METHOD FOR IDENTIFYING *LISTERIA MONOCYTOGENES* AND CULTURE MEDIUM**

(75) Inventors: Céline Roger-Dalbert, Vaux en Buggey (FR); Laurence Barbaux, Amberieu-en-Bugey (FR)

(73) Assignee: Biomerieux S.A., Marcy l'Etoile (FR)

( * ) Notice: Subject to any disclaimer, the term of this patent is extended or adjusted under 35 U.S.C. 154(b) by 412 days.

(21) Appl. No.: 10/432,048

(22) PCT Filed: Nov. 19, 2001

(86) PCT No.: PCT/FR01/03627

§ 371 (c)(1),
(2), (4) Date: May 18, 2003

(87) PCT Pub. No.: WO02/40705

PCT Pub. Date: May 23, 2002

(65) Prior Publication Data

US 2004/0142412 A1    Jul. 22, 2004

(30) Foreign Application Priority Data

Nov. 17, 2000   (FR) .................................. 00 14892

(51) Int. Cl.
  *C12Q 1/00*   (2006.01)
  *C12Q 1/04*   (2006.01)
  *C12Q 1/08*   (2006.01)

(52) U.S. Cl. .................. 435/34; 435/35; 424/94.1; 424/94.5; 424/94.6

(58) Field of Classification Search ............... 424/94.1, 424/94.6, 94.5; 435/34, 35
See application file for complete search history.

(56) References Cited

U.S. PATENT DOCUMENTS 5,364,767 A    11/1994  Flowers et al. ............... 435/39
5,962,251 A    10/1999  Rambach ..................... 435/34
6,130,057 A *  10/2000  Gosnell et al. ............... 435/32
6,350,588 B1 *  2/2002  Roth et al. .................... 435/34

FOREIGN PATENT DOCUMENTS

| FR | 2 697 028 | 4/1994 |
| JP | 09-500791 | 1/1997 |
| WO | WO94/09152 | 4/1994 |
| WO | WO99/04032 | 1/1999 |

OTHER PUBLICATIONS

Barclay et al., "Haemolysins and extracellular enzymes of *Listeria monocytogenes* and *L. ivanovii*," 30 *J. Med. Microbiol* 111 (1989).
Kerouanton et al., "Comparison of five typing methods for the epidemiological study of *Listeria monocytogenes*," 43 *Int'l J. Food Microbiol.* 61 (1998).
Cox et al., "Enhanced haemolysis agar (EHA)—an improved selective and differential medium for isolation of *Listeria monocytogenes*," 8 *Food Microbiol.* 37 (1991).
Mobashery et al., "Conscripting β-Lactamase for Use in Drug Delivery. Synthesis and Biological Activity of a Cephalosporin $C_{10}$-Ester of an Antibiotic Dipeptide," 108 *J. Am. Chem. Soc.* 1685 (1986).
Groves et al., "Separation of Pathogenic from Apathogenic *Listeria monocytogenes* by Three In Vitro Reactions," *J.Clin.Microbiol.* 559 (1977).

* cited by examiner

*Primary Examiner*—Ruth A Davis
(74) *Attorney, Agent, or Firm*—James C. Lydon

(57) ABSTRACT

A substrate which can be used for the direct identification of pathogenic bacteria belonging to the genus *Listeria* by detecting an esterase activity other than Phosphatidyl Inositol-specific Phospholipase C (PI-PLC), an esterase which is specific to the species *Listeria monocytogenes*. The use of two substrates, one as described above and the other specific for all or some members of the genus *Listeria*, and a reaction medium containing such a substrate or such a combination of substrates are disclosed. An identification method which exploits such culture media is also disclosed. The invention is particularly applicable in the field of diagnosis.

13 Claims, No Drawings

METHOD FOR IDENTIFYING *LISTERIA MONOCYTOGENES* AND CULTURE MEDIUM

This application is a U.S. National Stage of International Application PCT/FR01/03627, filed Nov. 19, 2001 and published on May 23, 2002 in the French Language.

DESCRIPTION

This invention concerns a chromogenic substrate which can be used for the direct identification of pathogenic bacteria belonging to the genus *Listeri*, more precisely those of the species *Listeria monocytogenes*.

The invention also concerns using a combination of two substrates, one substantially specific for the species *Listeria monocytogenes*, and the other either specific or not for the genus *Listeria*. It also concerns a reaction medium containing such a substrate or such a combination of substrates. Finally, it concerns an identification method exploiting such culture media.

For many years, special substrates have been used to determine whether certain enzyme activities typical of microorganisms are present or not. Through the use of specific substrates, it is possible—on the basis of whether a reaction takes place or not—to characterize the nature of a group of microorganisms, or distinguish between different strains and/or species belonging to a given genus.

Synthetic enzyme substrates such as those exploited in this invention are made up of two different parts: the first part is specific to the enzyme activity being tested for and will hereafter be referred to as the target part; the second part acts as a marker and will hereafter be referred to as the marker part.

Such special substrates may be either fluorescent or chromogenic. In fact, the second marker part or the product of its reaction with one or more other compounds becomes fluorescent or chromogenic when it is no longer bound to the first target part (in this context, refer to Patent Application PCT/FR99/00781 filed on behalf of the applicant).

Isolating and identifying the bacterium *Listeria monocytogenes* is a major problem in safety monitoring in both the food industry and medical bacteriology. Among all the bacterial species belonging to the genus *Listeria*, only *Listeria monocytogenes* is known to be pathogenic in humans. It can cause listeriosis, a condition which is sometimes mortal (in 25 to 35% of cases) in the immunodeficient, very young children and pregnant women. Other *Listeria* species are non-pathogenic, or are only pathogenic in animals. Such is the case in particular for *Listeria ivanovii*.

Although the danger of listeriosis has diminished in recent years in most developed countries, modern society demands ever more stringent safety and, even if sporadic cases are accepted, more widespread outbreaks are not.

However, in France, for example, risk management policy tends to focus on the products further down the line (e.g. contamination levels in finished products) rather than components higher up in the production process (the infection of livestock). As a result, between 15 and 60% of all poultry carcasses, between 3 and 36% of all pig carcasses, and between 7 and 28% of all cow carcasses are contaminated by *Listeria*.

Therefore, when it comes to human bacterial infection, it is important to be able to make a definitive distinction between *Listeria monocytogenes* and the other, non-pathogenic members of the genus *Listeria*.

Distinction has traditionally been made between different *Listeria* spp. by using selective culture media. Two particular selective media are in the most widespread use: Palcam (Van Netten et al., J. Food Microbiol. (1988), 6, pp. 187-188) and Oxford (Curtis et al., Lett. Appl. Microbiol. (1989), 8, pp. 85-98). All species belonging to the genus *Listeria* can be detected using these media. Typical colonies are obtained which must subsequently be identified by means of further tests—microscopic and/or biochemical and/or immunologic and/or genetic—to check whether or not the colony corresponds to the species *Listeria monocytogenes*.

These extra experiments both slow down and increase the cost of testing. Furthermore, they require many different reagents and necessitate trained technicians. Finally, since picking the colonies to be identified is a random process, the extra experiments often introduce mistakes, or at least compromise the accuracy and reliability of the result. This is a particularly acute problem when the number of colonies of *Listeria monocytogenes* on the isolation medium is much lower than the number of colonies of other *Listeria* species.

The Applicant's Patent EP-B-0.496.680 describes a bacteriological test method to differentiate the species *Listeria monocytogenes* from other bacterial species which belong to the genus *Listeria*. According to this method, use is made of an identification medium containing a chromogenic or fluorogenic substrate which is hydrolyzed by an enzyme called Glycine aminopeptidase. The medium used may also contain a substrate which can be fermented and/or a substrate which can be reduced and/or a substrate which can be enzymatically hydrolyzed, such as the substrate for $\alpha$-mannosidase, the chemical conversion of which makes it possible to characterize the *Listeria* species present in the test sample.

This useful approach has one major drawback in that the species *Listeria monocytogenes* is the only one not to express Glycine aminopeptidase activity. It is therefore possible to identify all *Listeria* species except the one member of the genus which is pathogenic, namely *Listeria monocytogenes*. Trying to detect *Listeria monocytogenes* by virtue of the absence of a certain activity is not very reliable since such a negative test lacks specificity because of the possibility of mutation and because another species might not be expressing its normal pattern of activity due to stress.

Methods based on using chromogenic media to detect *Listeria* genus-specific $\beta$-glucosidase activity have been developed. Moreover, other techniques based on chromogenic media can be used to distinguish between *Listeria monocytogenes* and *Listeria ivanovii* from other *Listeria* species by assaying phosphatidylinositol phospholipase C (PI-PLC) activity.

It has been shown that certain species of the genus *Listeria* (such as *Listeria monocytogenes* and *Listeria ivanovii*) secrete PI-PLC into the culture medium (Leimeister-Wächter et al., Mol. Microbiol. (1991) 5(2), pp. 361-366; J. Mengaud et al., Mol. Microbiol. (1991) 5(2), pp. 367-372; and Goldfine et al., Infection and Immunity (1992) 60(10), pp. 4059-4067). It is also known that these two species can be identified using indirect methods (Notermans et al., App. and Env. Microbiology (1991), vol. 57 n°9, pp. 2666-2670.

Patent Application WO-A-99/04032 describes a culture medium containing a chromogenic substrate which is specific for *Listeria monocytogenes* and *Listeria ivanovii*, in the form of a phosphatidylinositol derivative such as the ammonium salt of 5-Bromo-4-chloro-3-indolyl-myo-inositol-1-phosphate. This affords direct detection of both these species in a single step, and therefore makes it possible to distinguish these two from all other *Listeria* species.

Bacteriological detection tests based on PI-PLC are also dealt with in the following documents:

WO-A-98/38332 which focuses on a method and a detection test for PI-PLC, based on the cleavage of a substrate by the enzyme, one of the residues of said substrate being chromogenic and making it possible to identify pathogenic *Listeria*, and WO99/48899 which describes a fluorogenic substrate based on 4-methylumbelliferone which is used to detect the PI-PLC activity expressed by a number of different species, namely *Clostridium* spp., *Listeria ivanovii*, *Staphylococcus aureus*, *Bacillus cereus*, *Bacillus thuringiensis* as well as *Listeria monocytogenes*.

In this document, attention is drawn to the fact that phospholipase C activity is not specific for *Listeria monocytogenes* since it is also found in other species, including another *Listeria* species, namely *Listeria ivanovii*.

However, it should be noted that esterase substrates are more easily and more cheaply synthesized than substrates for PI-PLC. Moreover, the advantage of using a chromogenic substrate (rather than a natural one) is that visual detection is easier, i.e. it is easier to distinguish colored colonies than it is to visualize a halo surrounding colonies. This advantage furthermore applies to cultures containing different microorganisms in that each colony has its own specific color, whereas a halo could spread out below two disparate colonies.

The purpose of this invention is to offer a detection method which makes it possible to differentiate the species *Listeria monocytogenes* from all other *Listeria* species. This is achieved by detecting at least one metabolic activity which has not hitherto been used either to detect *Listeria* or to differentiate *Listeria monocytogenes* from other species belonging to the genus *Listeria*. This activity is an esterase which is expressed far more strongly by *Listeria monocytogenes* than by other species in the genus. In addition, at least one other activity is assayed, namely an activity which is expressed by all or some *Listeria* such as a saccharidase, a phosphatase or an aminopeptidase, which enhances the contrast between the color of colonies of *Listeria monocytogenes* and that of colonies of other species belonging to the same genus. This makes it possible to distinguish *Listeria monocytogenes* from *Listeria ivanovii* et *Listeria innocua*, which are the species most commonly isolated, and which have enzyme profiles closely resembling that of *Listeria monocytogenes*.

To this effect, this invention concerns a substrate which can be used to directly identify pathogenic bacteria belonging to the genus *Listeria*, characterized in that it detects a *Listeria monocytogenes*-specific esterase activity, an esterase activity which is distinct from PI-PLC activity.

Thus although PI-PLC is an esterase, *Listeria ivanovii* is esterase negative despite being PI-PLC positive; therefore it could be confused with *Listeria monocytogenes*. In contrast to the background art and methods based on the detection of PI-PLC activity which do not differentiate *Listeria monocytogenes* from other *Listeria* species, this invention makes it possible to detect *Listeria monocytogenes* in a more specific way.

According to a preferred embodiment, the esterase activity is a specific enzyme activity, i.e. it cleaves the ester linkage between the marker part and the target part of the substrate.

According to a preferred embodiment, the linkage cleaved is an ester bond between an alcohol group on the marker part and an organic acid which constitutes the target.

According to a preferred embodiment, the marker part consists of a chromogenic molecule such as indoxyl which could be constituted by one of the following constituents:

5-Bromo-3-indoxyl, or
5-Bromo-4-chloro-3-indoxyl, or
6-Chloro-3-indoxyl, or
5-Bromo-6-chloro-3-indoxyl, or
6-Bromo-3-indoxyl.

According to a preferred embodiment, the target part consists of a fatty acid with a carbon chain containing between 2 and 20 carbon atoms, preferably between 4 and 10 carbon atoms.

Preferably, the substrate is either 5-Bromo-4-chloro-3-indolyl butyrate, 5-Bromo-4-chloro-3-indolyl octanoate, 5-Bromo-4-chloro-3-indolyl nonanoate or 5-Bromo-4-chloro-3-indolyl decanoate.

According to a modified embodiment, the substrate is paired with at least one other substrate making it possible to detect at least one other enzyme activity expressed by all or some *Listeria* species.

In the case in which there are two substrates, the substrate to detect esterase activity other than PI-PLC gives a color which is different from that given by the other enzyme activity which is different from the above-mentioned esterase activity.

According to a preferred embodiment, the other enzyme activity expressed by all or some *Listeria* species is a saccharidase, a phosphatase or an aminopeptidase.

Preferably, the marker part of the other substrate is based on:
5-Bromo-3-indoxyl, or
5-Bromo-4-chloro-3-indoxyl, or
6-Chloro-3-indoxyl, or
5-Bromo-6-chloro-3-indoxyl, or
6-Bromo-3-indoxyl.

With respect to -Chloro-3-indoxyl, such a molecule is particularly well described in Patent U.S. Pat. No. 5,364,767 in which it is essentially associated withN-Acetyl-β-D-galactosaminide, with N-Acetyl-β-D-glucosaminide, with Butyrate, with Octanoate, with the salt of p-toluidine phosphate, with Sulfate or with β-D-Glucopyranoside. It can also be based on 5-Bromo-6-chloro-3-indoxyl.

According to a modified embodiment, the other substrate consists of:
5-Bromo-6-chloro-3-indolyl-β-D-glucoside, or
6-Chloro-3-indolyl-β-D-glucoside, or
6-Chloro-3-indolyl-β-D-cellobioside, or
6-Chloro-3-indolyl-N-acetyl-β-D-glucosaminide, or
6-Chloro-3-indolyl-α-D-mannoside, or
6-Chloro-3-indolylphosphate.

This invention also concerns a reaction medium which allows the direct identification of *Listeria monocytogenes*, which exploits one or two substrates as defined above.

More precisely, the substrate which detects the esterase activity other than PI-PLC is at a concentration of between 20 mg/l and 3 g/l, or preferably between 50 mgL and 1 g/l, or preferably between 100 and 600 mg/l, or about 250 mg/l.

More precisely, the substrate which detects the other activity such as a saccharidase, a phosphatase or an aminopeptidase is at a concentration of between 10 mg/l and 500 mg/l, preferably between 50 and 300 mg/l, and more preferably still between 100 and 200 mg/l.

The medium is either liquid or semi-solid (with agar).

According to a modified embodiment, the medium includes a means of distinguishing *Listeria monocytogenes* from *Listeria welshimeri* and *Listeria seeligeri*, namely:
the addition of at least one acidified carbohydrate (e.g. Xylose and/or D-Tagatose) by *Listeria welshimeri* and *Listeria seeligeri* and not by *Listeria monocytogenes*, or the addition of at least one acidified carbohydrate by *Listeria monocytogenes* and possibly *Listeria innocua* and/or *Listeria ivanovii* and/or *Listeria grayii*.

the addition of at least one substrate to detect saccharidase activity (β-maltosidase) and/or phosphatase and/or aminopeptidase activity (L-glycine aminopeptidase) specific at least to *Listeria welshimeri* and *Listeria seeligeri* but not *Listeria monocytogenes*, or the addition of a natural Phospholipase (PLC) substrate, such as Phosphatidylinositol (PI) and/or Phosphatidylcholine (PC).

According to a particular embodiment, the medium includes a selective means of differentiating *Listeria monocytogenes* from at least the following species:
*Staphylococcus aureus*,
*Bacillus thuringiensis*,
*Enterococcus faecalis*,
*Escherichia coli*,
*Pseudomonas aeruginosa*, and
*Candida albicans*.

According to a preferred embodiment, the selective means is constituted by one of the following compounds:
Lithium chloride
Ceftazidime,
Amphotericin B,
Fosfomycin, and/or
Colistin.

This invention furthermore concerns a method for identifying pathogenic bacteria belonging to the species *Listeria monocytogenes*, comprising the following steps:
seeding of a culture medium as described above with a specimen suspected of containing the pathogenic bacteria,
incubation of the culture medium seeded with the specimen, and
determination of the presence of said pathogenic bacteria by virtue of the color and intensity typical of the substrate(s).

According to a modified embodiment, said specimen suspected of containing pathogenic bacteria is preliminarily concentrated prior to seeding on the culture medium, as defined above.

According to another modified embodiment of the method, whether or not said pathogenic bacteria are present is determined by virtue of the color and intensity typical of the substrate(s) after a period of 18 to 24 hours of incubation.

Finally, the invention proposes using a substrate consisting of a target part as defined above and an inhibitory part which specifically inhibits *Listeria monocytogenes* when it is released.

This invention therefore essentially concerns the differentiation of *Listeria monocytogenes* from other species belonging to the genus *Listeria*.

Esterase enzyme activity is a good marker for differentiating the species *Listeria monocytogenes* from other species belonging to the genus *Listeria*, apart from the more specific esterase activity referred to as PI-PLC.

Thus, the background art described above demonstrates the lack of specificity of PI-PLC (which is specific for a certain type of lipid) vis-à-vis differentiating the species *Listeria monocytogenes* and *Listeria ivanovii*, for example. PI-PLC hydrolyzes Phosphatidylinositol derivatives at a point between the Glycèrol and the inorganic Phosphate. In the case of a chromogenic substrate, the enzyme cleaves between the marker part and the inorganic Phosphate bound to the Inositol, as illustrated below.

Esterases according to this invention hydrolyze lipids containing one or more fatty acids with a chain preferably containing between 7 and 10 carbon atoms. These esterases hydrolyze ester bonds between an alcohol and an organic fatty acid, as illustrated below.

EXPERIMENT 1

Testing Several Esterase Substrates with the Same Chromogenic Marker but Fatty Acids with Different Chain Lengths The chromogenic esterase substrates tested were:
5-Bromo-3-indolyl octanoate, hereafter referred to as Blue-C8,
5-Bromo-3-indolyl nonanoate, hereafter referred to as Blue-C9, and
5-Bromo-3-indolyl decanoate, hereafter referred to as Blue-C10, A stock solution of each substrate at a concentration of 40 g/l was made up in a mixture of 40% Dimethylsulfoxide and 60% Polyoxyethylenesorbitan Monolaurate (Tween 20). An appropriate volume was added to three Columbia-type media while cooling to give a final substrate concentration of 250 mg/l. These dishes were divided into three areas and then each area was inoculated with a suspension (density=0.5 McFarland) of microorganisms taken from either the Applicant's own collection or the ATCC. The dishes were incubated for 48 hours at 37° C. The colonies which grew were examined by eye after 24 and 48 hours of incubation. Both the color and the intensity of the color of the colonies were recorded. The results are presented in Table 1 below.

TABLE 1

Testing several esterase substrates with the same chromogenic marker but containing fatty acids with different chain lengths

|  |  | with Blue-C8 | | with Blue-C9 | | with Blue-C10 | |
| --- | --- | --- | --- | --- | --- | --- | --- |
| Strain | IT | C | I | C | I | C | I |
| *Listeria monocytogenes* ATCC 19115 | 24 h | gray | 1 | gray | 1 | gray | 0.5 |
|  | 48 h | gray | 2 | gray | 2 | gray | 1 |
| *Listeria monocytogenes* ATCC 19117 | 24 h | gray | 1 | gray | 1 | gray | 0.5 |
|  | 48 h | gray | 2 | gray | 1.5 | gray | 1 |
| *Listeria monocytogenes* 092 | 24 h | gray | 1.5 | gray | 1 | gray | 1 |
|  | 48 h | gray | 2.5 | gray | 2 | gray | 2 |
| *Listeria innocua* 166 | 24 h | gray | 0.3 | — | — | — | — |
|  | 48 h | gray | 1 | gray | 0.5 | gray | 0.5 |
| *Listeria innocua* ATCC 33090 | 24 h | gray | 0.3 | — | — | — | — |
|  | 48 h | gray | 0.5 | gray | 0.3 | gray | 0.3 |
| *Listeria innocua* 171 | 24 h | — | — | — | — | — | — |
|  | 48 h | gray | 0.3 | gray | 0.3 | gray | 0.3 |
| *Listeria seeligeri* 011 | 24 h | — | — | — | — | — | — |
|  | 48 h | gray | 0.5 | gray | 0.5 | gray | 0.5 |
| *Listeria welshimeri* 078 | 24 h | gray | 0.5 | gray | 0.5 | — | — |
|  | 48 h | gray | 1 | gray | 1 | gray | 0.5 |
| *Listeria grayi* ATCC 19120 | 24 h | — | — | — | — | — | — |
|  | 48 h | — | — | — | — | — | — |
| *Listeria ivanovii* 018 | 24 h | — | — | — | — | — | — |
|  | 48 h | — | — | — | — | — | — |
| *Listeria ivanovii* 025 | 24 h | — | — | — | — | — | — |
|  | 48 h | — | — | — | — | — | — |

In Table 1 above, as in the following Tables, C represents the color of the colonies after incubation, I represents the intensity of the color, and the symbol "-" corresponds to the absence of color or intensity; finally, IT defines the incubation time. It should be noted that the intensity of the color is scored on an arbitrary scale but one which is consistent for all the biological specimens and media tested. This scale is valid for this experiment as well as all those that follow. It can be defined in the following way:
0 corresponds to no activity,
0.1 corresponds to a trace of color,
0.5 corresponds to very pale coloration, 1 corresponds to clear but low-intensity coloration,
1.5 corresponds to a degree of coloration intermediate between scores 1 and 2,
2 corresponds to clear coloration of moderate intensity,
2.5 corresponds to a degree of coloration intermediate between scores 2 and 3,
3 corresponds to intense coloration,
3.5 corresponds to a degree of coloration intermediate between scores 3 and 4,
4 corresponds to very intense coloration.

Only strains of *L. monocytogenes, L. innocua, L. seeligeri* and *L. welshimeri* gave a gray color: these strains therefore express an esterase activity. It is possible to distinguish-whatever the length of the fatty acid chain being tested-a difference of about 1 unit in the intensity given by *L. monocytogenes* strains (the higher scores) and the intensities given by strains of *L. innocua, L. welshimeri* and *L. seeligeri*.

6-Chloro-3-indolyl octanoate, hereafter referred to as Pink-C8, and

5-Bromo-6-chloro-3-indolyl octanoate, hereafter referred to as Magenta-C8,

A stock solution of each substrate at a concentration of 40 g/l was made up in a mixture of 40% Dimethylsulfoxide and 60% Tween 20. An appropriate volume was added to four Columbia-type media while cooling to give a final substrate concentration of 250 mg/l. These dishes were divided into three areas and then each area was inoculated with a suspension (density=0.5 McFarland) of microorganisms taken from either the Applicant's own collection or the ATCC. The dishes were incubated for 48 hours at 37° C. The colonies which grew were examined by eye after 24 and 48 hours of incubation. Both the color and the intensity of the color of the colonies were recorded. The results are presented in Table 2 below.

TABLE 2

Results obtained with several esterase substrates with different Indoxyl-based chromogenic markers and with octanoic acid as the fatty acid

| Strain | Medium IT | with Blue-C8 C | I | with X-C8 C | I | with Pink-C8 C | I | with Magenta-C8 C | I |
|---|---|---|---|---|---|---|---|---|---|
| *Listeria monocytogenes* ATCC 19115 | 24 h | gray | 1 | turquoise | 2.5 | pink | 0.5 | purple | 2 |
|  | 48 h | gray | 2 | turquoise | 3 | pink | 1 | purple | 3 |
| *Listeria monocytogenes* ATCC 19117 | 24 h | gray | 1 | turquoise | 2 | pink | 0.5 | purple | 1.5 |
|  | 48 h | gray | 2 | turquoise | 3 | pink | 1 | purple | 3.5 |
| *Listeria monocytogenes* 092 | 24 h | gray | 1.5 | turquoise | 3 | pink | 1.5 | purple | 3 |
|  | 48 h | gray | 2.5 | turquoise | 3.5 | pink | 2 | purple | 3 |
| *Listeria innocua* 166 | 24 h | gray | 0.3 | turquoise | 0.3 | — | — | purple | 2 |
|  | 48 h | gray | 1 | turquoise | 0.5 | pink | 0.3 | purple | 3 |
| *Listeria innocua* ATCC 33090 | 24 h | gray | 0.3 | turquoise | 0.3 | — | — | purple | 1 |
|  | 48 h | gray | 0.5 | turquoise | 0.5 | pink | 0.5 | purple | 2 |
| *Listeria innocua* 171 | 24 h | — | — | — — | | — — | | purple | 0.5 |
|  | 48 h | gray | 0.3 | turquoise | 0.3 | pink | 0.3 | purple | 3 |
| *Listeria ivanovii* 018 | 24 h | — | — | — — | | — — | | — — | |
|  | 48 h | — | — | — — | | — — | | — — | |
| *Listeria ivanovii* 025 | 24 h | — | — | — — | | — — | | — — | |
|  | 48 h | — | — | — — | | — — | | — — | |

However, in the following examples, only the results obtained with substrates based on the octanoate and the nonanoate will be given.

Moreover, it can be seen that only strains of *Listeria monocytogenes* give any color after 24 hours. It is therefore possible to differentiate *Listeria monocytogenes* from other *Listeria* species on the basis of incubation temperature.

EXPERIMENT 2

Testing Several Esterase Substrates with Different Indoxyl-based Chromogenic Markers and with Octanoic Acid as the Fatty Acid The chromogenic esterase substrates tested were:
5-Bromo-3-indolyl octanoate, hereafter referred to as Blue-C8,
5-Bromo-4-chloro-3-indolyl octanoate, hereafter referred to as X-C8, Whatever substrate was used, a difference in intensity was observed between strains of *Listeria monocytogenes* and strains of *Listeria innocua*. However, the difference was more significant for the markers 5-Bromo-4-chloro-3-indoxyl and 5-Bromo-3-indoxyl.

Beter contrast and stronger intensity was obtained with the marker that gave a turquoise color, namely 5-Bromo-4-chloro-3-indoxyl.

EXPERIMENT 3

Detecting an Esterase Activity in Liquid Medium

The chromogenic esterase substrates tested were:
5-Bromo-4-chloro-3-indolyl acetate, hereafter referred to as X-C2,
3-Indolyl acetate, hereafter referred to as Y-C2,
5-Bromo-4-chloro-3-indolyl butyrate, hereafter referred to as X-C4, 5-Bromo-4-chloro-3-indolyl octanoate, hereafter referred to as X-C8,
5-Bromo-6-chloro-3-indolyl octanoate, hereafter referred to as M-C8, and
6-Chloro-3-indolyl octanoate, hereafter referred to as R-C8.

These substrates were lyophilized in the wells of API-type strips (Registered Trademark). Before use, the substrates contained in the wells were resuspended in an agar-free Columbia-type inoculation medium. These wells were then inoculated with a suspension (density=2 McFarland) of microorganisms taken from either the Applicant's own collection or the ATCC. The strips were incubated for 8 hours at 37° C. The colonies which grew were examined by eye after 4, 6 and 8 hours of incubation.

The intensity of the color of the colonies was recorded. The results are presented in Table 3 below.

TABLE 3

Results obtained with several esterase substrates with different Indoxyl-based chromogenic markers and with fatty acids containing chains of different lengths

| Strain | Medium IT | X-C2 I | Y-C2 I | X-C4 I | X-C8 I | M-C8 I | R-C8 I |
|---|---|---|---|---|---|---|---|
| *Listeria monocytogenes* | 4 h | 3 | 3 | 1 | — | — | — |
| ATCC 19115 | 6 h | 4 | 4 | 2 | 1 | — | — |
|  | 8 h | 4 | 4 | 3 | 1.5 | 0.5 | — |
| *Listeria monocytogenes* | 4 h | 3 | 4 | 2 | — | — | — |
| 092 | 6 h | 4 | 4 | 2 | 1 | — | — |
|  | 8 h | 4 | 4 | 3 | 1.5 | 0.5 | — |
| *Listeria innocua* 171 | 4 h | 4 | 3 | 0.5 | — | — | — |
|  | 6 h | 4 | 3 | 1 | — | — | — |
|  | 8 h | 4 | 4 | 2 | — | — | — |
| *Listeria innocua* 166 | 4 h | 3 | 3 | 0.5 | — | — | — |
|  | 6 h | 4 | 3 | 1 | — | — | — |
|  | 8 h | 4 | 4 | 2 | — | — | — |
| *Listeria welshimeri* 023 | 4 h | 3 | 3 | 0.5 | — | — | — |
|  | 6 h | 4 | 4 | 1 | — | — | — |
|  | 8 h | 4 | 4 | 2 | — | — | — |
| *Listeria seeligeri* 011 | 4 h | 3 | 3 | 0.5 | — | — | — |
|  | 6 h | 3 | 3 | 1 | 0.5 | — | — |
|  | 8 h | 4 | 4 | 2 | 0.5 | — | — |
| *Listeria ivanovii* 018 | 4 h | 3 | 3 | 0.5 | — | — | — |
|  | 6 h | 3 | 4 | 1 | — | — | — |
|  | 8 h | 4 | 4 | 2 | — | — | — |
| *Listeria grayi* ATCC 19120 | 4 h | 2 | 3 | 0.5 | — | — | — |
|  | 6 h | 2 | 4 | 1 | — | — | — |
|  | 8 h | 3 | 4 | 2 | — | — | — |

In liquid medium, substrates with a chain of under 4 carbon atoms do not differentiate between different *Listeria* species. In contrast, in the operating conditions tested, the substrates X-C4 and X-C8 gave a contrast in color between *L. monocytogenes* and other species belonging to the same genus. In practice, only *L. welshimeri* and *L. seeligeri* also gave any color, but the color that they gave was of very low intensity. It is possible to imagine setting a threshold for a positive response at 1. Test strains which gave a reading of below 1 would be considered as negative; strains giving a reading of over 1 would be considered as positive. Thus, in the present case, it would mean that it is a strain of *L. monocytogenes*.

EXPERIMENT 4

Simultaneous Detection of an Esterase Activity and a Saccharidase Activity in Semi-solid Medium Various pairs of a chromogenic esterase substrate with a chromogenic saccharidase substrate were tested, as follows:

5-Bromo-3-indolyl octanoate and 6-Chloro-3-indolyl-β-D-glucoside, which corresponds to Pair 1, 5-Bromo-3-indolyl octanoate and 6-Chloro-3-indolyl-β-D-cellobioside, which corresponds to Pair 2, 5-Bromo-3-indolyl octanoate and 6-Chloro-3-indolyl-N-acetyl-β-D-glucosarinide, which corresponds to Pair 3, 5-Bromo-3-indolyl octanoate and 6-Chloro-3-indolyl-α-D-mannoside, which corresponds to Pair 4, 5-Bromo-4-chloro-3-indolyl octanoate and 6-Chloro-3-indolyl-β-D-glucoside, which corresponds to Pair 5, 5-Bromo-4-chloro-3-indolyl octanoate and 6-Chloro-3-indolyl-β-D-cellobioside, which corresponds to Pair 6, 5-Bromo-4-chloro-3-indolyl octanoate and 6-Chloro-3-indolyl-N-acetyl-β-D-glucosaminide, which corresponds to Pair 7, and 5-Bromo-4-chloro-3-indolyl octanoate and 6-Chloro-3-indolyl-α-D-mannoside, which corresponds to Pair 8.

A stock solution of each esterase substrate at a concentration of 40 g/l was made up in a mixture of 40% Dimethylsulfoxide and 60% Tween 20. And a stock solution of each saccharidase substrate was made up in Dimethylsulfoxide. An appropriate volume of the stock solution of the esterase substrate corresponding to each of the pairs described above was added to one of eight Columbia-type media while cooling to obtain a final substrate concentration of 250 mg/l. In parallel, an appropriate volume of the stock solution of the saccharidase substrate corresponding to each of the pairs described above was added to each of the eight media in order to obtain a final concentration of between 100 and 200 mg/l (depending on the substrate). These dishes were divided into three areas and then each area was inoculated with a suspension (density=0.5 McFarland) of microorganisms taken from either the Applicant's own collection or the ATCC. The dishes were incubated for 48 hours at 37° C. The colonies which grew were examined by eye after 24 and 48 hours of incubation.

Both the color and the intensity of the color of the colonies were recorded. The results are presented in Table 4 below.

TABLE 4

Results obtained using different pairs of chromogenic substrates to simultaneously detect an esterase activity and a saccharidase activity in a semi-solid medium

| Strain | Medium IT | Pair 1 C | I | Pair 2 C | I | Pair 3 C | I | Pair 4 C | I |
|---|---|---|---|---|---|---|---|---|---|
| Listeria monocytogenes ATCC 19115 | 24 h | gray | 2 | purple-gray | 2 | purple | 3 | purple | 3 |
|  | 48 h | purple-gray | 3 | purple-gray | 3 | purple | 3.5 | purple | 3.5 |
| Listeria monocytogenes ATCC 19117 | 24 h | purple-gray | 2 | purple-gray | 2 | purple | 3 | purple | 2 |
|  | 48 h | purple-gray | 3 | purple-gray | 3 | purple-gray | 3.5 | purple | 3.5 |
| Listeria monocytogenes 092 | 24 h | purple-gray | 3 | purple-gray | 2 | purple | 3 | purple | 3 |
|  | 48 h | purple-gray | 3.5 | purple-gray | 3 | purple-gray | 3.5 | purple | 3.5 |
| Listeria innocua 166 | 24 h | mauve | 1.5 | pink-gray | 1.5 | mauve | 2 | mauve | 2 |
|  | 48 h | mauve | 3 | pink-gray | 2 | purple | 3 | purple | 3 |
| Listeria innocua ATCC 33090 | 24 h | mauve | 1 | pink-gray | 1 | mauve | 2 | mauve | 2 |
|  | 48 h | mauve | 3 | pink-gray | 2 | purple | 3 | purple | 3 |
| Listeria innocua 171 | 24 h | mauve | 1 | pink-gray | 1 | mauve | 1.5 | mauve | 1.5 |
|  | 48 h | mauve | 3 | pink-gray | 2 | purple | 3 | purple | 3 |
| Listeria ivanovii 018 | 24 h | pink | 1 | pink | 1 | pink | 1 | pink | 1 |
|  | 48 h | pink | 2 | pink | 2 | pink | 2 | pink | 2 |
| Listeria ivanovii 025 | 24 h | pink | 1 | pink | 1 | pink | 1 | pink | 1 |
|  | 48 h | pink | 2 | pink | 2 | pink | 2 | pink | 2 |

| Strain | Medium IT | Pair 5 C | I | Pair 6 C | I | Pair 7 C | I | Pair 8 C | I |
|---|---|---|---|---|---|---|---|---|---|
| Listeria monocytogenes ATCC 19115 | 24 h | blue | 3 | blue | 3 | blue | 3 | blue | 3 |
|  | 48 h | blue-gray | 3.5 | blue-gray | 3.5 | blue-gray | 3.5 | blue-gray | 3.5 |
| Listeria monocytogenes ATCC 19117 | 24 h | blue | 3 | blue | 3 | blue | 3 | blue | 3 |
|  | 48 h | blue-gray | 3.5 | blue-gray | 3.5 | blue-gray | 3 | blue-gray | 3.5 |
| Listeria monocytogenes 092 | 24 h | blue | 3 | blue | 3 | blue | 3 | blue | 3 |
|  | 48 h | blue-gray | 3.5 | blue-gray | 3.5 | blue-gray | 3.5 | blue-gray | 4 |
| Listeria innocua 166 | 24 h | purple | 1 | blue-purple | 1 | mauve | 1 | purple | 2 |
|  | 48 h | purple | 2 | blue-purple | 2 | mauve | 2 | purple | 3 |
| Listeria innocua ATCC 33090 | 24 h | purple | 1 | blue-purple | 2 | mauve | 1 | purple | 2 |
|  | 48 h | purple | 3 | blue-purple | 3 | mauve | 3 | purple | 3 |
| Listeria innocua 171 | 24 h | purple | 1 | blue-purple | 2 | mauve | 1 | purple | 2 |
|  | 48 h | purple | 3 | blue-purple | 2 | mauve | 3 | purple | 3 |
| Listeria ivanovii 018 | 24 h | pink | 1 | pink | 1 | pink | 1 | pink | 1 |
|  | 48 h | pink | 2 | pink | 2 | pink | 2 | pink | 2 |
| Listeria ivanovii 025 | 24 h | pink | 1 | pink | 1 | pink | 1 | pink | 1 |
|  | 48 h | pink | 2 | pink | 2 | pink | 2 | pink | 2 |

Whatever pair of substrates was tested, a color difference was observed between strains of *Listeria monocytogenes* and strains of *Listeria innocua* and *Listeria ivanovii*.

The best contrast was obtained with 5-Bromo-4-chloro-3-indolyl nonanoate together with a saccharidase substrate based on 6-Chloro-3-indolyl, whatever the target activity. Therefore, in principle any of the various esterase substrates can be paired with a saccharidase, be it an α-polysaccharidases or a β-polysaccharidase.

However, it can be seen that the best results were obtained using 6-Chloro-3-indolyl-β-D-giucoside, 6-Chloro-3-indolyl-N-acetyl-β-D-glucosaminide and 6-Chloro-3-indolyl-α-D-mannoside.

EXPERIMENT 5

Simultaneous Detection of an Esterase Activity and a Phosphatase Activity in Semi-solid Medium Volumes of two stock solutions were successively added into a semi-solid Columbia-type medium while cooling: 5-Bromo-4-chloro-3-indolyl octanoate (X-C8) (final concentration in the medium: 250 mg/l) and 6-Chloro-3-indolyl phosphate (Pink P) (final concentration in the medium: 750 mg/l). The stock 5-Bromo-4-chloro-3-indolyl octanoate solution was prepared as in the previous examples, and that of 6-Chloro-3-indolyl phosphate was made up at a concentration of 50 g/l in Dimethylsulfoxide.

These dishes were divided into three areas and then each area was inoculated with a suspension (density=0.5 McFarland) of microorganisms taken from either the Applicant's own collection or the ATCC. The dishes were incubated for 48 hours at 37° C. The colonies which grew were examined by eye after 24 and 48 hours of incubation.

Both the color and the intensity of the color of the colonies were recorded. The results are presented in Table 5 below.

TABLE 5 simultaneous detection of an esterase activity and a phosphatase activity

| | Medium | X-C8 and Pink P | |
| --- | --- | --- | --- |
| Strain | IT | C | I |
| Listeria monocytogenes ATCC 19115 | 24 h | blue-gray | 2 |
| | 48 h | blue-gray | 3 |
| Listeria monocytogenes 092 | 24 h | blue | 2 |
| | 48 h | blue-gray | 3 |
| Listeria innocua 166 | 24 h | pink-gray | 0.5 |
| | 48 h | pink-gray | 2 |
| Listeria innocua 171 | 24 h | pink | 0.5 |
| | 48 h | pink | 1.5 |
| Listeria ivanovii 022 | 24 h | pink-gray | 0.5 |
| | 48 h | pink-gray | 3 |
| Listeria welshimeri 081 | 24 h | blue-gray | 3 |
| | 48 h | blue-gray | 3 |
| Listeria seeligeri 011 | 24 h | blue-gray | 0.5 |
| | 48 h | blue-gray | 2 |
| Listeria grayi ATCC 19120 | 24 h | gray | 0.5 |
| | 48 h | gray | 1 |

Simultaneous testing of both these activities make it possible to differentiate between two groups of Listeria, on the one hand L. monocytogenes, L. seeligeri and L. welshimeri, and on the other hand L. grayi, L. innocua and L. ivanovii. This detection system can be improved by adjusting the composition of the medium (as will be explained in Experiment 6) so that it becomes possible to differentiate L. monocytogenes from all other species belonging to the genus Listeria.

EXPERIMENT 6

Differentiation of Listeria monocytogenes from Listeria welshimeri and Listeria seeligeri in a Semi-solid Medium Containing an Esterase Substrate and a Saccharidase Substrate The following pair of chromogenic esterase substrate with chromogenic saccharidase substrate was tested: 5-Bromo-4-chloro-3-indolyl octanoate and 6-Chloro-3-indolyl-N-acetyl-β-D-glucosaminide Media and stock substrate solutions were prepared as in the previous examples. This basic medium was divided into four portions into which were added respectively:

40 g/l Xylose corresponding to Medium 1, 40 g/l Tagatose corresponding to Medium 2, a mixture of 45 g/l carbohydrates with 30 g/l Xylose and 15 g/l Tagatose corresponding to Medium 3, a mixture of 65 g/l carbohydrates with 35 g/l Xylose and 30 g/l Tagatose corresponding to Medium 4, These dishes were divided into three areas and then each area was inoculated with a suspension (density=0.5 McFarland) of microorganisms taken from the Applicant's collection. The dishes were incubated for 48 hours at 37° C. The colonies which grew were examined by eye after 24 and 48 hours of incubation.

Both the color and the intensity of the color of the colonies were recorded. The results are presented in Table 6 below.

TABLE 6

Enhancement of the specificity for L. monocytogenes vis-à-vis L. welshimeri and L. seeligeri by the addition of a very high concentration of carbohydrate

| | Medium | Medium 1 | | Medium 2 | | Medium 3 | | Medium 4 | |
| --- | --- | --- | --- | --- | --- | --- | --- | --- | --- |
| Strain | IT | C | I | C | I | C | I | C | I |
| Listeria monocytogenes 079 | 24 h | blue | 2 | blue-gray | 1 | blue-gray | 1 | blue-gray | 0.5 |
| | 48 h | blue-gray | 3 | blue-gray | 3 | blue-gray | 3 | blue-gray | 3 |
| Listeria monocytogenes 081 | 24 h | blue | 2 | blue-gray | 1 | blue-gray | 1 | blue-gray | 0.5 |
| | 48 h | blue-gray | 3 | blue-gray | 3 | blue-gray | 3 | blue-gray | 3 |
| Listeria innocua 29 | 24 h | mauve | 2 | pink | 1 | pink | 1 | mauve | 0.5 |
| | 48 h | mauve | 2 | mauve | 3 | mauve | 3 | mauve | 3 |
| Listeria seeligeri | 24 h | turquoise | 2 | turquoise | 0.5 | turquoise | 0.5 | turquoise | 0.5 |

TABLE 6-continued

Enhancement of the specificity for *L. monocytogenes*
vis-à-vis *L. welshimeri* and *L. seeligeri* by the addition
of a very high concentration of carbohydrate

| Strain | Medium IT | Medium 1 C | I | Medium 2 C | I | Medium 3 C | I | Medium 4 C | I |
|---|---|---|---|---|---|---|---|---|---|
| 012 | 48 h | turquoise | 3 | blue-gray | 3 | turquoise | 3 | turquoise | 2 |
| *Listeria welshimeri* 023 | 24 h | turquoise | 2 | turquoise | 0.5 | turquoise | 0.5 | turquoise | 0.5 |
|  | 48 h | blue-gray | 3 | blue-gray | 3 | turquoise | 3 | turquoise | 3 |
| *Listeria ivanovii* 025 | 24 h | pink | 1 | pink | 1 | pink | 1 | pink | 1 |
|  | 48 h | pink | 2 | pink | 2 | pink | 2 | pink | 2 |
| *Listeria grayi* 078 | 24 h | pink | 3 | pink | 3 | pink | 3 | pink | 3 |
|  | 48 h | pink | 3 | pink | 3 | pink | 3 | pink | 3 |

Adding a very high concentration of carbohydrate (over 40 g/l) makes it possible to make a distinction between *L. monocytogenes* and all other *Listeria* species, and this purely on the basis of color. Nevertheless, it has been shown that it is possible to make a distinction between species using lower concentrations (down to 10 g/l) as is detailed in Patent FR-B-2.708.285. However here, unlike in this above-mentioned Patent, the color change is due to the inhibition of an enzyme, not due to a derived color different from the basic color of the marker.

EXPERIMENT 7

Addition of Selective Agents to Inhibit Gram-positive Bacteria Other than *Listeria* and to Inhibit Gram-negative Bacteria and Yeast The basic Columbia-type medium contains:
5-Bromo-4-chloro-3-indolyl octanoate (250 mg/l) prepared from a stock solution in a mixture of 40% Dimethylsulfoxide and 60% Polyoxyethylenesorbitan Monolaurate (Tween 20),
5-Bromo-6-chloro-3-indolyl-?-N-acétylglucosaminide (150 mg/l) prepared from a stock solution in DMSO,
Xylose (10 g/l) and Tagatose (5 g/l), and
a selective medium defined as follows: Lithium chloride (5 g/l), Ceftazidime (20 mg/l), Amphotericin B (4 mg/l), Fosfomycin (10 mg/l) and Colistin (5 mg/l).

These dishes were divided into three areas and then each area was inoculated with a suspension (density=0.5 McFarland) of microorganisms taken from the Applicant's collection. The dishes were incubated for 48 hours at 37° C. The colonies which grew were examined by eye after 24 and 48 hours of incubation. Both the color and the intensity of the color of the colonies were recorded. The results are presented in Table 7 below.

TABLE 7

Results obtained with media either containing or not containing selective agents

| Strain | Medium IT | no selective agent C | I | with selective agents C | I |
|---|---|---|---|---|---|
| *Listeria monocytogenes* 028 | 24 h | blue | 1 | blue | 1 |
|  | 48 h | blue | 3 | blue | 3 |
| *Listeria monocytogenes* 023 | 24 h | blue | 2 | blue | 2 |
|  | 48 h | blue | 3.5 | blue | 3 |
| *Listeria innocua* 036 | 24 h | mauve | 1.5 | mauve | 1 |
|  | 48 h | mauve | 3 | mauve | 2 |
| *Listeria ivanovii* 018 | 24 h | pink | 1 | — | — |
|  | 48 h | pink | 2 | mauve | 1 |
| *Listeria welshimeri* 081 | 24 h | turquoise | 1 | turquoise | 1 |
|  | 48 h | turquoise | 3 | turquoise | 2 |
| *Staphylococcus aureus* 029 | 24 h | green | 2 | — | — |
|  | 48 h | green | 3.5 | — | — |
| *Bacillus thuringiensis* 072 | 24 h | turquoise | 0.5 |  |  |
|  | 48 h | turquoise | 1 |  |  |
| *Enterococcus faecalis* 117 | 24 h | turquoise | 0.5 | — | — |
|  | 48 h | turquoise | 1 | — | — |
| *Escherichia coli* 006 | 24 h | colorless | — | — | — |
|  | 48 h | colorless | — | — | — |
| *Pseudomonas aeruginosa* 003 | 24 h | green | 0.5 | — | — |
|  | 48 h | green | 2 | — | — |
| *Candida albicans* 077 | 24 h | turquoise | 0.5 | — | — |
|  | 48 h | turquoise | 1 | — | — |

In Table 7 above, C represents the color of colonies after incubation, I represents the intensity of this color, the symbol "—" signals the absence of any growth, and finally IT corresponds to incubation time. It should be noted that the intensity of the color is scored on an arbitrary scale but one which is consistent for all the biological specimens and media tested.

It can be seen that, in the presence of selective agents, all the interfering bacteria and yeast present (i.e. any microorganisms which are not *Listeria*) fail to grow, i.e. are inhibited. The presence of selective agents does not affect the color of the *Listeria* strains tested.

This experiment also shows that, even without any selective agents, it is possible to differentiate between *Listeria monocytogenes* on the one hand and interfering bacteria and yeast on the other hand, which is not true with the substrates, culture media and reagents described in the background art.

The invention claimed is:

1. A composition for the direct identification of pathogenic bacteria belonging to the species *Listeria monocytogenes*, said composition comprising a first substrate comprising a target part comprising a fatty acid having a carbon chain containing between 2 and 20 carbon atoms and a marker part, and wherein said first substrate is cleavable by an esterase activity other than Phosphatidyl Inositol-specific Phospholipase C (PI-PLC), and wherein said esterase activity is specific for *Listeria monocytogenes* and not specific for other members of the genus *Listeria* further comprising a second substrate comprising a target part and a marker part, wherein said second substrate detects at least one other enzyme activity expressed by all or some *Listeria* species, and wherein the marker part of said first substrate is different from the marker part of said second substrate.

2. The composition of claim 1, wherein the esterase activity is a specific enzyme activity.

3. The composition of claim 2, wherein said first substrate is cleavable at an ester bond between an alcohol group on the marker part and an organic acid which comprises the target part.

4. The composition of claim 3, wherein the marker part of said first substrate comprises a chromogenic molecule.

5. The composition of claim 4, wherein said first substrate is a member selected from the group consisting of 5-Bromo-4-chloro-3-indolyl butyrate, 5-Bromo-4-chloro-3-indolyl octanoate, 5-Bromo-4-chloro-3-indolyl nonanoate and 5-Bromo-4-chloro-3-indolyl decanoate.

6. The composition of claim 4, wherein said chromogenic molecule contains indoxyl.

7. The composition of claim 6, wherein said indoxyl is selected from the group consisting of
5-Bromo-3-indoxyl,
5-Bromo-4-chloro-3-indoxyl,
6-Chloro-3-indoxyl,
5-Bromo-6-chloro-3-indoxyl, and
6-Bromo-3-incloxyl.

8. The composition of claim 2, wherein said specific enzyme activity cleaves a linkage between said marker part and said target part of the first substrate.

9. The composition of claim 1, wherein the first substrate which is cleaved by an esterase activity other than that of PI-PLC produces a color which is different from that produced by said other enzyme activity.

10. The composition of claim 1, wherein said other enzyme activity expressed by all or some *Listeria* species is a saccharidase, a phosphatase or an aminopeptidase.

11. The composition of claim 1, wherein the marker part of said second substrate contains a constituent selected from the group consisting of:
5-Bromo-3-indoxyl,
5-Bromo-4-chloro-3-indoxyl,
6-Chloro-3-indoxyl,
5-Bromo-6-chloro-3-indoxyl, and
6-Bromo-3-indoxyl.

12. The composition of claim 11, wherein the marker part of the second substrate is selected from the group consisting of 5-Bromo-6-chloro-3-indolyl-β-D-glucoside, 6-Chloro-3-indolyl -β-D-glucoside, 6-Chloro-3-indolyl-β-D-cellobioside, 6Chloro-3-indolyl-N-acetyl-β-D-glucosaminide, 6-Chloro-3-indolyl-α-D-mannoside and 6-Chloro-3-indolylphosphate.

13. The composition of claim 1, wherein said carbon chain of said target part of said first substrate contains 4-10 carbon atoms.

* * * * *

UNITED STATES PATENT AND TRADEMARK OFFICE
CERTIFICATE OF CORRECTION

PATENT NO. : 7,270,978 B2
APPLICATION NO. : 10/432048
DATED : September 18, 2007
INVENTOR(S) : Celine Roger-Dalbert and Laurence Barbaux It is certified that error appears in the above-identified patent and that said Letters Patent is hereby corrected as shown below:

The following corrections are requested:

In column 5, between lines 62 and 63, insert:

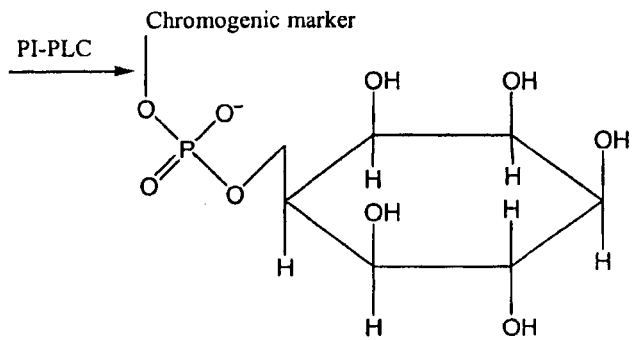

In column 5, after line 67, insert:

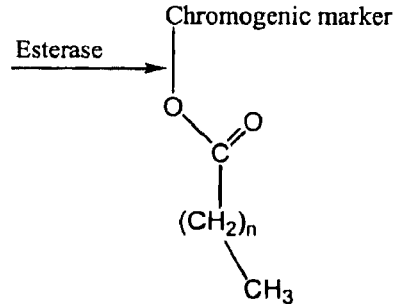

Signed and Sealed this

Seventeenth Day of June, 2008

JON W. DUDAS
*Director of the United States Patent and Trademark Office*